United States Patent [19]

Patchett et al.

[11] 4,431,821
[45] Feb. 14, 1984

[54] FLUORINATED TRYPTAMINES

[75] Inventors: Arthur A. Patchett, Cranford; Janos Kollonitsch, Westfield, both of N.J.

[73] Assignee: Merck & Co., Inc., Rahway, N.J.

[21] Appl. No.: 285,168

[22] Filed: Jul. 20, 1981

Related U.S. Application Data

[62] Division of Ser. No. 140,376, Apr. 14, 1980, which is a division of Ser. No. 886,602, Mar. 16, 1979, abandoned, which is a continuation-in-part of Ser. No. 802,350, Jun. 1, 1977, abandoned.

[51] Int. Cl.³ .......................................... C07D 209/16
[52] U.S. Cl. .................................. 548/508; 548/341; 564/355; 562/444
[58] Field of Search ..................... 260/326.15; 548/504

[56] References Cited

U.S. PATENT DOCUMENTS 4,325,961  4/1982  Kollonitsch et al. ...... 260/326.14 T

*Primary Examiner*—Paul M. Coughlan, Jr.
*Assistant Examiner*—D. B. Springer
*Attorney, Agent, or Firm*—Gabriel Lopez; Daniel T. Szura; Hesna J. Pfeiffer

[57] ABSTRACT

Novel 1-fluoromethyl-substituted alkyl amines are disclosed. The novel compounds have biological activity including decarboxylase inhibition.

7 Claims, No Drawings

FLUORINATED TRYPTAMINES

This is a division of application Ser. No. 140,376, filed Apr. 14, 1980 which in turn is a divisional application of Ser. No. 886,602, filed Mar. 16, 1979, now abandoned, which in turn is a continuation-in-part of application Ser. No. 802,350, filed June, 1, 1977, now abandoned.

BACKGROUND OF THE INVENTION

The present invention is concerned with novel 1-fluoromethyl substituted alkylamines.

Various nonfluorinated substituted alkylamines such as histamine, 2-(3,4-dihydroxyphenyl)ethylamine (dopamine), tyramine, amphetamine and hydroxyamphetamine, are known. These compounds exhibit various physiological activities and have various clinical utilities (See D. M. Aviado "Sympathomimetic Drugs", Charles C. Thomas, Publisher, 1970).

1-Fluoromethyl substituted alkyl amines have been discovered. These amines have decarboxylase inhibiting activity.

SUMMARY OF THE INVENTION

1-Fluoromethyl substituted alkylamines and salts thereof.

DESCRIPTION OF THE PREFERRED EMBODIMENTS

An embodiment of the present invention is compounds having the formula

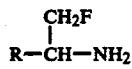
$$\text{R—CH—NH}_2 \quad \text{I}$$
(with CH$_2$F on the CH)

wherein R is a substituted C$_1$–C$_4$ alkyl group.

The pharmaceutically acceptable acid addition salts of the formula I compounds are also included. In general, the salts are those of the formula I base with a suitable organic or inorganic acid. Preferred inorganic acid salts are the hydrohalides e.g., hydrochlorides, hydroiodides, hydrobromides; the sulfates, and the phosphates. The hydrohalides, and especially the hydrochlorides, are more preferred.

The formula I compounds have a chiral center and may occur in optically active forms i.e., as optical isomers. These isomers are designated conventionally by the symbols L and D, + and −, l and d, S and R or combinations thereof. Where the compound name or formula has no isomer designation, the name or formula includes the individual isomers, mixtures thereof and racemates.

The compounds having the S-isomer configuration are, in general, preferred.

R is a substituted alkyl group exemplified by

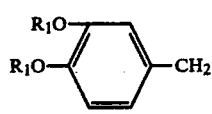

where R$_1$ is H or C$_2$–C$_6$ alkanoyl e.g., CH$_3$—CO, CH$_3$(CH$_2$)$_4$—CO, (CH$_3$)$_3$C—CO and the like;

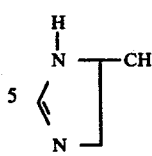

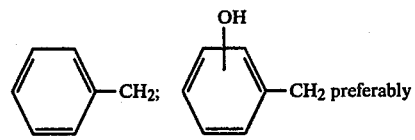

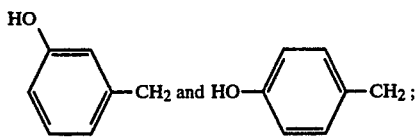

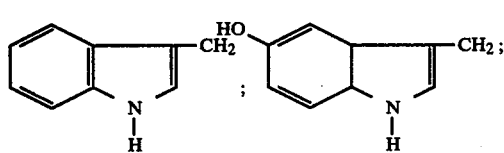

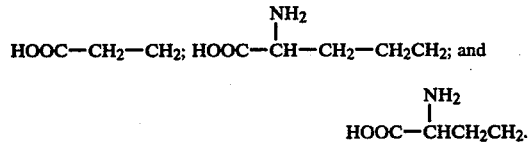

Preferred compounds of formula I are those where R is

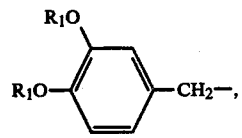

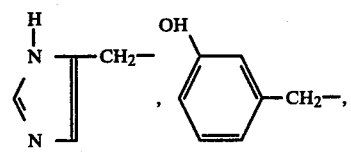

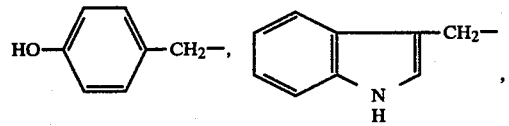

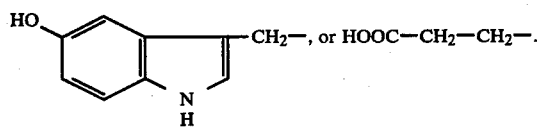

Compounds which are particularly preferred have the formula

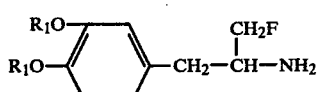
II

More preferred formula II compounds are those wherein $R_1$ is hydrogen; formula II compounds having the S-isomer configuration are especially preferred.

Another particularly preferred compound has the formula

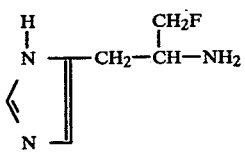   III

Another preferred compound has the formula

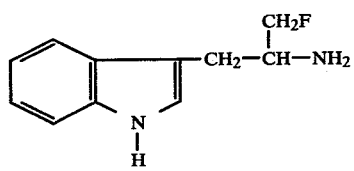   IV

Another preferred compound has the formula

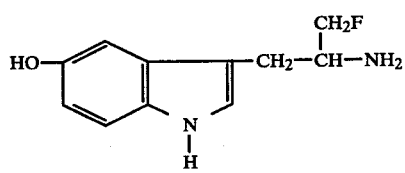   V

Still another preferred compound has the formula

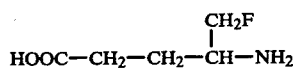   VI

The compounds of the present invention have potent decarboxylase inhibiting activity. Decarboxylases are enzymes which act on α-amino acid substrates, effecting decarboxylation to produce the corresponding amine. This action is illustrated by the following equation:

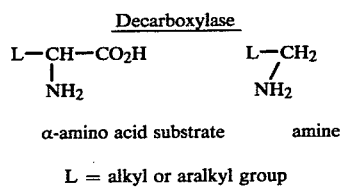

L = alkyl or aralkyl group

By inhibiting this decarboxylation, the biosynthetic pathway to a number of biologically significant amines can be modulated or inhibited with physiologically useful consequences. For example, α-fluoromethyl dopamine inhibits dopa decarboxylase and can be used in combination with dopa to potentiate the latter's usefulness in the treatment of Parkinson's disease.

The present compounds also are substantially specific in their decarboxylase inhibition activity, that is an α-fluoromethyl alkylamine generally inhibits the decarboxylation of the corresponding non α-fluoromethyl-α amino acid. For example, α-fluoromethyl dopamine inhibits the decarboxylation of dopa; α-fluoromethyl histamine will inhibit the decarboxylation of histidine; 4-FM-GABA (4-fluoromethyl-4-amino-butyric acid) inhibits glutamic acid decarboxylase; etc.

Because of this specificity and potency as decarboxylase inhibitors, the present compounds are also useful as diagnostic tools to determine the presence and importance of the corresponding decarboxylase in relation to diseases or to the functioning of biological systems. For example, the role of catechol amines in certain CNS functions can be studied by inhibiting their biosynthesis with an appropriate α-fluoromethyl-alkylamine; α-fluoromethyl-tryptamine displays antihypertensive activity; and the study and treatment of ulcers can be advanced through modulation of histamine biosynthesis using α-fluoromethyl histamine.

Representative compounds have been determined to have decarboxylase inhibiting activity using a conventional in-vitro assay.

A representative compound, S-(and R) 1-fluoromethyl-2(3,4-dihydroxyphenyl)ethylamine, also referred to as α-fluoromethyl dopamine, was found to effect a pressor response in rats. This indicates that some of the present compounds may also be useful for treating hypotension in humans.

4-FM-GABA displays CNS activities, including sedative and antidepressant indications.

The compounds of the present invention may be prepared using any convenient method.

One such useful process involves the reaction of an α-hydroxymethyl-alkyl amine with $SF_4$ in liquid HF, as illustrated by the following equation:

The reaction is generally carried out at temperatures ranging from about $-80°$ C. to about $20°$ C. This general reaction is also referred to as fluorodehydroxylation and is described in the Journal of Organic Chemistry 40, 3809–10 (1975).

Another useful method for preparation of α-fluoromethyl amines involves photofluorination, e.g.:

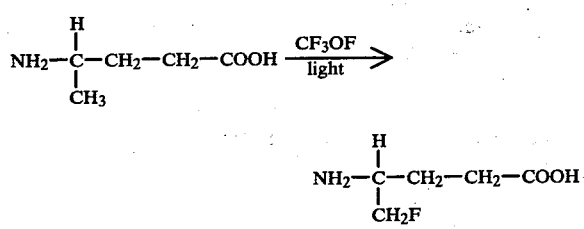

This process was described generally in J. Am. Chem. Soc. 98, 5591 (1976) and ibid. 92, 7494 (1970).

An acid addition salt of a compound of the present invention may be prepared by conventional treatment of the α-fluoromethyl amine with a useful acid generally in a suitable solvent.

A single enantiomer of the present compounds may be obtained by (1) resolving the fluoromethyl amine racemate using conventional resolution techniques or (2) resolving the precursor α-hydroxymethyl amine using conventional resolution techniques and then fluorodehydroxylating the precursor enantiomer. A conventional resolution technique may involve formation of a salt of the appropriate amine with an opticaly active acid and subsequently recovering the specific enantiomer from the salt.

Compounds of the formula

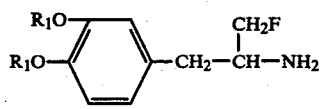

where $R_1$ is $C_2-C_6$ alkanoyl are prepared by acylating the corresponding compound where $R_1$ is hydrogen, in an acid medium to prevent acylation of the amino group. In general, conventional acylating agents and conditions are employed.

The following examples illustrate preparation of representative compounds of the present invention. All temperatures are in °C. Melting points are determined in open capillary and are uncorrected.

EXAMPLE 1

Synthesis of R-α-Fluoromethyl-Dopamine.HCl (a) Preparation of R-α-Hydroxymethyl-Dopamine.HCl Four and 55/100 g of sodium borohydride is suspended by stirring (magnetic stirring bar) with 250 ml of tetrahydrofuran (THF). To the stirred suspension there is added 6.7 g of $CaCl_2$ (powder), the mixture stirred for 30 minutes at room temperature, then refluxed under stirring for 90 minutes. To the $Ca(BH_4)_2$ solution thus obtained, a solution of 10.2 g of methyl ester of D-DOPA (DOPA=3,4-dihydroxy-phenylalanine) in 55 ml of THF is admixed. After 15 minutes at room temperature, the suspension is refluxed with continued stirring for 5½ hours. (Note: The whole operation described above was conducted under a protective blanket of dry $N_2$ gas.) The solvent is evaporated in vacuo and methanol (300 ml) is added with caution. After the gas evolution ceases, the solvent is removed by distillation in vacuo, fresh methanol is added again, then HCl gas is passed in until saturation. Solvent is removed again by evaporation in vacuo and the whole $CH_3OH$/HCl treatment is repeated. (These treatments split the borate complex formed in the reduction as well as removing the methyl borate). The residue is dissolved in $H_2O$, 109 ml of 0.55 M aq. $H_2SO_4$ is added and the mixture aged at 5° C. overnight. The $CaSO_4$ is added and the mixture aged at 5° C. overnight. The $CaSO_4.2H_2O$ is then removed by filtration, washed with water (10 ml) and isopropanol (2×30 ml). The combined filtrates were evaporated in vacuo to dryness, the solid residue is stirred with isopropanol (100 ml) for ½ h., filtered, cake washed with isopropanol (2×30 ml), the combined filtrates evaporated to dryness in vacuo. This crude product is further purified by elution chromatography (cation-exchange resin column made of 0.95 l AG50-X-8 resin, 200/400 mesh, H+ form). Effluent is monitored by LKB UVICORD II UV monitor. Elution is as follows:

| | |
|---|---|
| 0.4M aq. HCl, containing 7.5% methanol: | 5 l |
| 0.6M aq. HCl, containing 10% methanol: | 4.8 l |
| 0.7M aq. HCl, containing 10% methanol: | 2.1 l |
| 1.0M aq. HCl, containing 10% methanol: | 4.0 |
| Elution rate: | 0.6 l/hour. |

The product is located by the UV absorption monitor, which is connected with a chart recorder. The UV absorbing peak is released by the last solvent listed. The appropriate fractions are combined and evaporated to dryness in vacuo, to deliver the hydrochloride of R-α-hydroxymethyl-dopa-mine. For final purification this is recrystallized from isopropanol, to give crystalline product, m.p. 159°–160° C. $[\alpha]_D$: 19.5±0.5° (c, 1 in 1 M aq. HCl).

(b) Preparation of R-α-Fluoromethyl-Dopamine.HCl

One g of the product obtained under (a) is charged into a KEL-F ® reactor. HF gas is passed in while the reactor is immersed in a dry-ice-acetone bath, until a solution with 30 ml volume forms. The cooling bath is removed and the solvent evaporated by passing through a stream of $N_2$ gas. The residue thus obtained represents the HF salt of R-α-hydroxymethyl-dopamine. This is redissolved by condensing into the reactor HF again by cooling it in a dry-ice-acetone bath and passing in HF gas until a solution with volume 50 ml forms. $SF_4$ gas (1.5 ml, measured as liquid at −78° C.) is passed in then under continuous cooling and stirring and the solution left standing overnight, while the reactor is being kept in the cooling bath, but without replenishing dry ice. The solvent is removed the next morning by passing through a stream of $N_2$ and the residue is redissolved in 2.5 M aq. HCl (25 ml), evaporated to dryness and the residue purified by elution chromatography on a column made of cation-exchange resin (190 ml of Dowex 50 AG50-X-8, 200/400 mesh). Elution with water, followed by 0.5 M aq. HCl with 5% methanol (2 l), followed by 0.6 M aq. HCl with 10% methanol (4 l). UV absorption of the effluent is followed by LKB UVI-CORD II recording UV monitor. The effluent fractions containing UV absorbing material are evaporated to dryness in vacuo to deliver R-α-fluoromethyl-dopamine.HCl. 0.6 g of this crude product is dissolved in isopropanol (4 ml), treated with DARCO G-60, then 26 ml of ethyl acetate is added. The crystalline product is reflux once more in a similar manner, to give 0.545 g of pure HCl salt, m.p. 152-3° C. $[\alpha]_D$: 18.4±0.5 (C, 1 in 1 M aq. HCl).

EXAMPLE 2

Synthesis of S-α-Fluoromethyl-Dopamine.HCl

S-α-Fluoromethyl dopamine.HCl is synthesized in an entirely analogous manner as described in Example 1 for the R isomer; however to obtain the S isomer, the methyl ester of L-DOPA is employed as starting material. The intermediate S-hydroxymethyl dopamine has a melting point of 159°-60° C.; $[\alpha]_D$: −20.1±0.5° (C, 1 in 1 M aq. HCl). The S-α-fluoromethyl-dopamine.HCl obtained from this fluorodehydroxylation, has a m.p.=151-3° C. $[\alpha]_D$: −19.2±0.5° (C, 1 in 1 M aq. HCl).

EXAMPLE 3

Synthesis of R-α-Fluoromethyl-Histamine

One g of D-histidinol is placed into a KEL-F reactor; the reactor is immersed into a dry-ice-acetone cooling bath and HF gas is passed in until a volume of 40 ml collects. $SF_4$ gas is passed in (2.0 ml, measured as liquid, at −78° C.) and the mixture kept at −78° C. for 5 hours. The cooling bath is removed and the solvent evaporated by passing $N_2$ gas through it. The residue is dissolved in cc. aq. HCl (15 ml), the solution is evaporated to dryness in vacuo to yield substantially pure R-α-fluoromethyl-histamine hydrochloride-hydrofluoride salt. For transformation into the dihydrochloride salt, this product is dissolved in water and charged onto a cation-exchange resin column Dowex 50-X-8 (ml resin, H+ form). The column is washed first with H₂O until the effluent becomes neutral, then the product is eluted with 4 M aq. HCl (275 ml). This effluent is evaporated to dryness to deliver substantially pure R-α-fluoromethyl-histamine dihydrochloride. This is recrystallized by dissolving it in 40 ml of boiling ethanol 2BA, concentrating this solution by evaporation in vacuo to 15 ml volume and cooled (ice-bath) for 2 hours. The crystals formed are collected by filtration and dried in vacuo to give R-α-fluoromethyl-histamine dihydrochloride, m.p. 181–2°.

EXAMPLE 4

Synthesis of S-α-Fluoromethyl-Histamine

S-α-Fluoromethyl histamine.HCl is prepared from L-histidinol via the method described in Example 3 for R-α-fluoromethyl-histamine.2HCl, m.p. =182–83° C.

The free amines are obtained from the hydrochloride salts by conventional neutralization.

EXAMPLE 5

Synthesis of (S)-α-fluoromethyl-tryptamine

S(L)-Tryptophanol (0.7 g, 3.7 mmoles) was placed in a Kel-F reactor, cooled in a dry ice-acetone bath (−78° C.) and approximately 20 ml of anhydrous HF was condensed with stirring at −78° C. Sulfur tetrafluoride (approx. 1.5 ml, 26 mmoles) was added with stirring at −78° C. over a 15-minute period. The reaction mixture was stirred for 30 minutes at −78° C. and then the HF was blown off with a fast stream of N₂ over a 2.5-hr. period at −78° C. The dark residue was dissolved in 25 ml 3 N HCl and evaporated to dryness at 25° C., in vacuo. The residue was dissolved in 10 ml H₂O, basified with 2.5 N NaOH, and the separated amine was extracted with 2×50 ml ether. The combined ether extracts were dried over MgSO₄ and evaporated to dryness in vacuo at room temperature. The crude product (4 spots, by TLC on silica gel plates developed with ethyl acetate-methanol-water 85:10:5) was chromatographed on silica gel H (E. Merck, 120 g.) using ethyl acetate-methanol-water 88:10:2 as the elution solvent. The desired product, (S)-α-fluoromethyl-tryptamine, was contained in fractions No. 31–60 (12 ml each). They were combined and evaporated to dryness to yield S-α-fluoromethyl-tryptamine characterized as the tartarate salt, by 300 MHz ¹H NMR, mass spectroscopy and microanalysis.

EXAMPLE 6

Synthesis of R-α-Fluoromethyl-tryptamine

Employing the procedure described in Example 5, but using R(D)-tryptophanol as starting material, R-α-fluoromethyl-tryptamine is obtained.

EXAMPLE 7

Synthesis of R,S-4-Fluoromethyl-4-Amino-butyric Acid

Eleven and 7/10 g of 4-methyl-4-amino-butyric acid is placed in a KEL-F reactor and dissolved in 200 ml of liquid HF; then CF₃OF gas is passed in while the reactor is immersed in a dry-ice/acetone cooling bath. The solution is irradiated (through a window on the top) by a 2500 W ultraviolet light source. (See J. of Am. Chem. Soc. 98, 5591–93 (1976) and ibid 92, 7494 (1970) for a general description of photofluorination).

First, 3 ml liquid C₃OF is allowed to evaporate and passed into the solution during a 70 minute period, followed by another 40 min. period with irradiation. Two additional 2 ml (liq.) increments of CF₃OF are passed into the reaction mixture with continuing irradiation, each in a time period of about 2 hours. The liquid HF is then removed by a stream of nitrogen gas. The residue is dissolved in 50 ml of 2.5 N aq. HCl and evaporated to dryness in vacuo. This treatment is repeated. The residue thus obtained is dissolved in 270 ml of water; 270 ml of conc. aq. HCl is added and the solution refluxed for 16 hours, then evaporated to dryness in vacuo, redissolved in 100 ml of water and chromatographed on a column of cation-exchange resin 3 1 of AG-50-X-8 (200–400 mesh) resin is employed in the H+ form. Elution: 18 liters of water, followed by 0.4 N aq. HCl. The effluent is monitored by UVICORD Model III ultraviolet absorption monitor, filter 206 nm. 22 ml fractions are collected. Fractions 410–610 are combined and evaporated to dryness in vacuo to deliver 4-fluoromethyl-4-amino-butyric acid hydrochloride. For liberation of the acid, the 4-FM-GABA.HCl is dissolved in water and passed through an AG-50-X-8 ion-exchange resin column (100 ml of resin). The column is first washed with water, then eluted with 2 N aq. NH₄OH. Evaporation of the NH₄OH solution in vacuo gives R,S-4-fluoromethyl-4-amino butyric acid. It is recrystallized from H₂O/ isopropanol and characterized by C-H-N-F analysis and ¹H and ¹⁹F NMR spectroscopy.

What is claimed is:

1. A compound of the formula

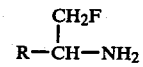

wherein R is

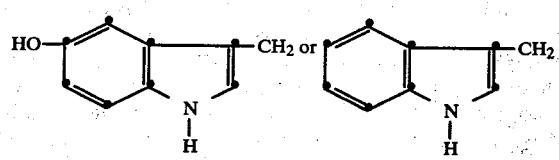

2. Pharmaceutically acceptable acid addition salts of the claim 1 compounds.

3. A compound of claim 1 having the S-isomer configuration.

4. A compound of claim 1 of the formula

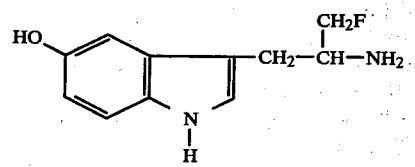

5. A compound of claim 4 having the S-isomer configuration.

6. A compound of clam 1 of the formula

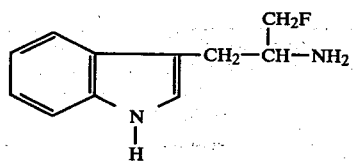

7. A compound of claim 6 having the S-isomer configuration.

* * * * *